United States Patent [19]

Kelso, Jr.

[11] Patent Number: 4,779,735
[45] Date of Patent: Oct. 25, 1988

[54] WOOD-PRESERVATIVE PACKAGE

[75] Inventor: William C. Kelso, Jr., Coldwater, Miss.

[73] Assignee: Mooney Chemicals, Inc., Cleveland, Ohio

[21] Appl. No.: 60,781

[22] Filed: Jun. 10, 1987

[51] Int. Cl.$^4$ .................................. B65D 73/00
[52] U.S. Cl. ................... 206/484; 206/210; 206/223; 206/440; 206/813; 427/397
[58] Field of Search ............ 206/210, 223, 440, 484, 206/484.2, 524.7, 813; 128/156; 427/397

[56] References Cited

U.S. PATENT DOCUMENTS

| | | | |
|---|---|---|---|
| 2,069,335 | 2/1937 | Salfisbery | 206/484 |
| 2,875,020 | 2/1959 | Ring | 21/7 |
| 2,904,467 | 9/1959 | Behr | 167/38.7 |
| 2,955,331 | 10/1960 | Nelson | 21/62 |
| 2,982,394 | 5/1961 | Novak | 206/524.7 |
| 3,149,943 | 9/1964 | Amador | 206/484 |
| 3,181,696 | 5/1965 | Reddin et al. | 206/484 |
| 3,199,945 | 8/1965 | Stutz | 21/62 |
| 3,501,339 | 3/1970 | Gurgiolo | 427/397 |
| 3,509,991 | 4/1969 | Hurst | 206/813 |
| 3,635,567 | 1/1972 | Richardson, Jr. | 206/813 |
| 3,692,469 | 9/1972 | Peace | 206/813 |
| 4,656,060 | 4/1987 | Krzyzewski | 427/397 |
| 4,731,267 | 3/1988 | Makus et al. | 428/35 |

FOREIGN PATENT DOCUMENTS 0152976 8/1985 European Pat. Off. .

OTHER PUBLICATIONS

Hunt, George M. et al, "Wood Preservation", Second Edition, McGraw-Hill Book Company, Inc. (1953), pp. 151–157.
Nicholas, Darrel D., Editor, "Wood Deterioration and Its Prevention by Preservative Treatments", vol. II, Syracuse University Press (1973), p. 282.
Bell System, "Preservative Treatment of Standing Poles", pp. 1–8.
Chapman Chemical Company, Product Bulletin for "Pol-Nu Pak".
Koppers Company, Inc., Product Data Sheet for "Tritox".
DeGroot, Rodney C., "Groundline Treatments of Southern Pine Posts", U.S. Dept. of Agriculture, Forest Products Lab. Res. Paper FPL409(8/81).
Osmose Wood Preserving Co. of Amer., Inc., Non-Titled brochure on Standing Pole Maintenance (1983).

*Primary Examiner*—David T. Fidei
*Attorney, Agent, or Firm*—Renner, Otto, Boisselle & Sklar

[57] ABSTRACT

A wood-preservative package or bandage is disclosed which comprises: a first flexible sheet; a wood-preservative material having a grease-like consistency arranged in a layer upon said first flexible sheet; a perforated flexible sheet overlying said preservative material and secured to the marginal edge of said first flexible sheet, the perforations in said perforated flexible sheet being of sufficient number and dimension to permit said wood-preservative material to pass through said perforations; and another flexible sheet overlying and secured to said perforated flexible sheet. This wood-preservative package is particularly suitable for treating poles used for supporting telephone lines, power transmission lines and the like that have been held in stock for extended periods of time and for the ground-line treatment of such poles.

26 Claims, 2 Drawing Sheets

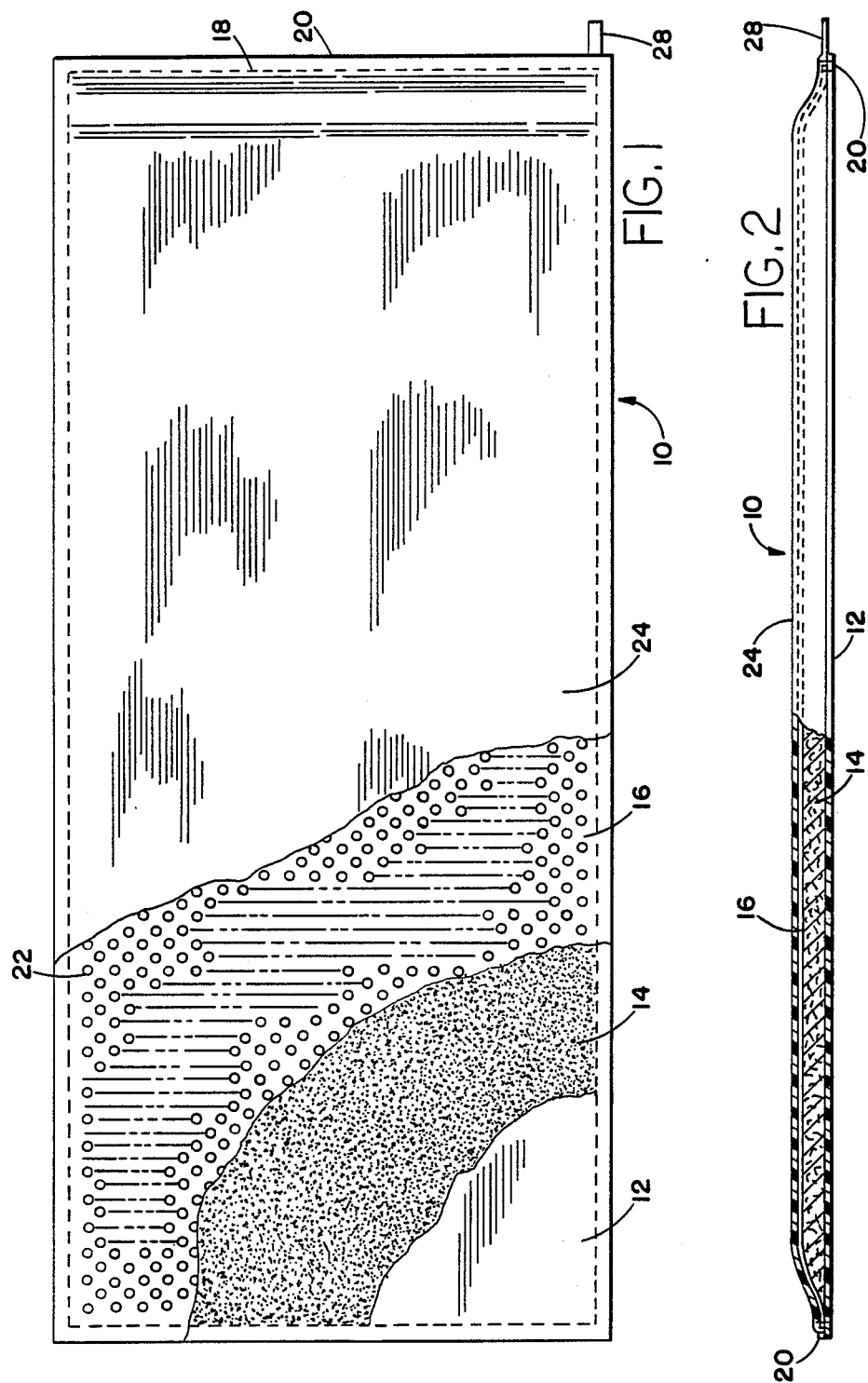

4,779,735

WOOD-PRESERVATIVE PACKAGE

TECHNICAL FIELD

This invention relates to wood-preservative packages and, more particularly, to wood-preservative packages or bandages which are particularly suitable for treating poles such as those used for supporting telephone wires, power transmission lines and the like that have been held in stock for extended periods of time and for the ground-line treatment of such poles.

BACKGROUND OF THE INVENTION

Various means have been provided for preventing the rotting or deterioration of wood in standing poles such as those used for supporting telephone wires, power transmission lines and the like. Standing poles of this type are usually treated before they are inserted into the ground. However, if the treatment is ineffective, or if the pole is subjected to unusual conditions, a rotting and deterioration of the wood may take place. The greatest deterioration usually takes place at or near the ground line. As this is the part of the pole which is subjected to greatest strain, the preservation of this portion of the pole is of utmost importance.

Various types of wood-preservative packages or bandages have been suggested for the ground-line treatment of standing poles. One of these types of packages consists of a coating of preservative material applied to a polyethylene-backed kraft paper. A thin sheet of polyethylene is removed at the time of pole treatment for direct contact with wood. Handling problems have resulted with these packages due to the fact that the wood-preservative material is toxic and the installer often ends up directly contacting it.

Another of these types of packages has a wood-preservative material applied to a supporting sheet material and a water-soluble film overlying the wood-preservative material. This package is wrapped around the pole with the water-soluble film in contact with the wood. The water-soluble film is not perforated and thus the package is only effective after it rains. Even when it rains, the rain may not be sufficient to completely dissolve the film, particularly below ground level, thereby preventing portions of the wood-preservative material from contacting the wood.

Wood-preservative packages are disclosed in U.S. Pat. Nos. 2,875,020; 2,955,331; and 3,199,945. U.S. Pat. No. 2,875,020 discloses a wood-preservative package comprising: a porous, fibrous, oil and water-permeable sheet; a layer on one side of said sheet of an inert oil-based carrier of grease-like consistency containing at least 2% pentachlorophenol; and a synthetic, resinous oil and water-impervious film completely enclosing the sheet and layer.

U.S. Pat. No. 2,955,331 discloses a wood preservative package comprising: a sheet of fibrous paper having a grease-resistant heat sealable coating thereon; a layer of wood-preservative material arranged in a layer upon said coating spaced from the edges of said sheet; a layer of fibrous tissue overlying said wood-preservative material and secured to said sheet outwardly of said preservative material layer; said sheet with its coating, said grease proof material and said layer of tissue being folded intermediate the ends of the sheet; the ends and side edges of said sheet being heat-sealed together, whereby when said sheet is unfolded, together with said preservative material and said tissue layer, and wrapped about a pole with said fibrous tissue layer against said pole, said tissue layer may act as a wick to transmit said preservative material to said pole, said preservative material comprising a greasy substance containing heavy fractions and less viscous fractions, said tissue restraining the heavier fractions of said material and permitting passage of said less viscous fractions.

U.S. Pat. No. 3,199,945 discloses a wood-preservative package comprising: an outer sheet of pliable grease resistant material; a layer of wood-preservative material arranged on said sheet and spaced from the edges thereof; said outer sheet and said layer of preservative material being folded intermediate the ends of said outer sheet forming a doubled edge at the outer sheet forming upper and lower sheet portions with the preservative material forming upper and lower preservative layers, the ends and side edges of said outer sheet being sealed together to form a seam with a space existing between the seam and the edges of said preservative layers; upper and lower separator sheets of porous separator material between said preservative layers for permitting separation of said layers, said upper sheet being severable along a severance line between the seam and said edges of the wood-preservative layers so that the sheet may be unfolded together with the layers of wood-preservative and the unfolded package may be placed against a wood surface, and an attachment strip in said space secured to the upper outer sheet between said severance line and the preservative material and extending from the edge of the upper separator sheet in said space so that said strip will lift the upper separator sheet as the upper outer sheet portion is raised after being severed along said severance line.

SUMMARY OF THE INVENTION

The present invention provides for a wood-preservative package or bandage comprising: a first flexible sheet; a wood-preservative material having a grease-like consistency arranged in a layer upon said first flexible sheet; a perforated flexible sheet overlying said preservative material and secured to the marginal edge of said first flexible sheet, the perforations in said perforated flexible sheet being of sufficient number and dimension to permit said wood-preservative material to pass through said perforations; and another flexible sheet overlying and secured to said perforated flexible sheet. This wood-preservative package is particularly suitable for treating poles used for supporting telephone lines, power transmission lines and the like that have been held in stock for extended periods of time and for the ground-line treatment of such poles.

BRIEF DESCRIPTION OF THE DRAWINGS

In the annexed drawings, like references indicate like parts or features:

FIG. 1 is a partially cut-away plan view of a wood-preservative package illustrating the invention in a particular form;

FIG. 2 is a partially cut-away side elevation of the wood-preservative package of FIG. 1;

DESCRIPTION OF THE PREFERRED EMBODIMENTS

Figure 3:
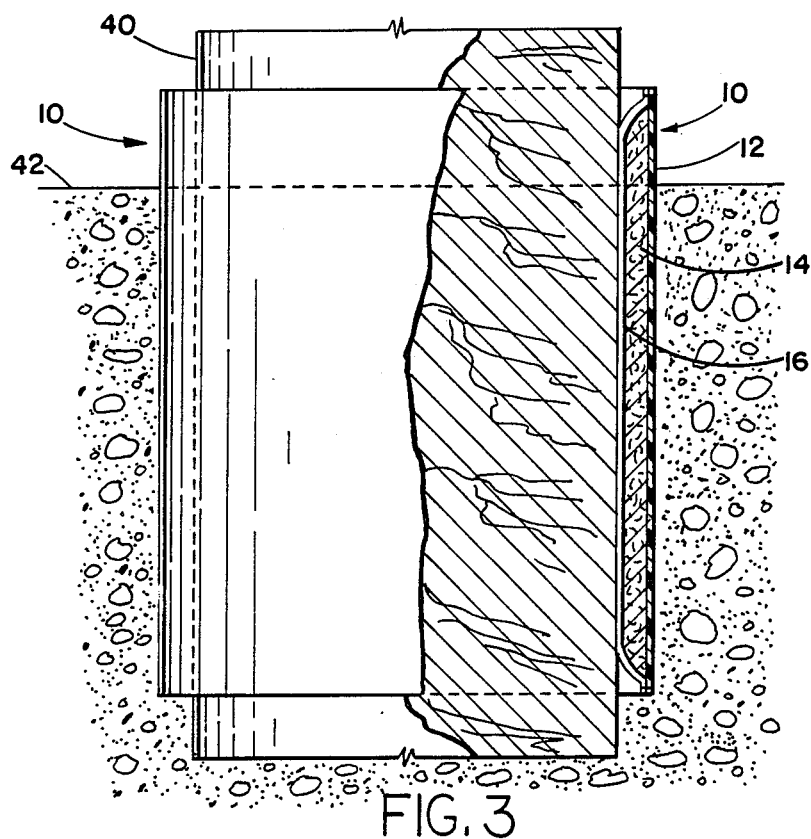
FIG. 3 is a partially cut-away, sectioned, side elevational view of a standing pole with the wood-preservative package of FIG. 1 wrapped around it.

Referring initially to FIGS. 1–3, the wood-preservative package or bandage of the present invention, which in its illustrated embodiment, is indicated generally by the reference numeral 10, comprises a first flexible sheet 12; a wood-preservative material 14 having a grease-like consistency arranged in a layer upon said first flexible sheet 12; a perforated flexible sheet 16 overlying said wood-preservative material 14 and secured to said first flexible sheet 12 by stitching 18 along the marginal edge 20 of flexible sheet 12, the perforations 22 in said perforated flexible sheet 16 being of sufficient number and dimension to permit said wood-preservative material 14 to pass through said perforations 22; and another flexible sheet 24 overlying and secured to said perforated flexible sheet 16, all as hereinafter further explained.

The flexible sheets 12 and 24 are preferably rectangular in shape and can be made of kraft paper or any water-insoluble polymeric sheet or film material. The water-insoluble polymeric sheet or film material is preferably polyethylene, polyvinyl chloride or polyvinylidene chloride. The kraft paper can optionally, and preferably, have a thin flexible coating or film of a water-insoluble polymeric material such as polyethylene, polyvinyl chloride, or polyvinylidene chloride on the side of the paper contacting the wood-preservative material 14.

The perforated flexible sheet 16 can be made of a water-soluble or water-insoluble polymeric sheet or film material. Examples of such water-soluble polymeric sheet or film materials include polyacrylic acid, and copolymers of an acrylate ester and another hydrophilic monomer (e.g., hydroxyethyl acrylate, 2-hydroxy-propyl acrylate and mixtures thereof). Examples of such water-insoluble polymeric sheet or film materials include polyethylene, polyvinyl chloride, polyvinylidene chloride, etc. The perforated sheet 16 can also be kraft paper with a thin flexible coating or film of a water-insoluble polymeric material (e.g., polyethylene, polyvinyl chloride, polyvinylidene chloride, etc.) on the side in contact with the wood-preservative material 14. The perforations 22 are preferably spaced at regular intervals to permit the wood-preservative material 14 to pass through said perforations and to contact the entire or substantially entire wood surface covered by the package 10.

Figure 4:
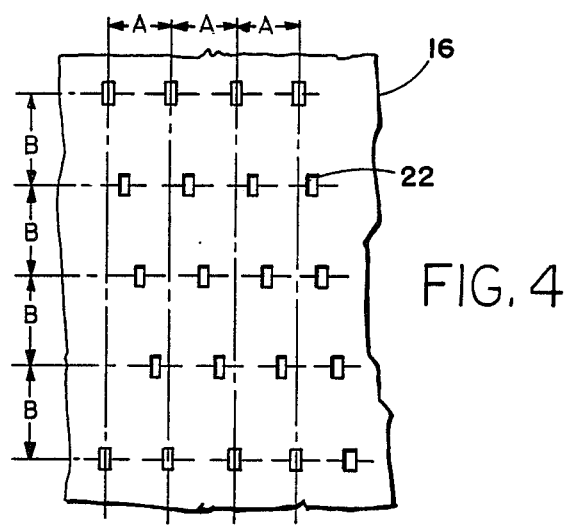
FIG. 4 is an enlarged partial plan view of a pattern of perforations that is useful with the perforated flexible sheet of the wood-preservative package illustrated in FIG. 1, the perforations illustrated in this pattern being rectangular while the perforations illustrated in FIG. 1 are circular.

A particularly advantageous arrangement for the perforations 22 is illustrated in FIG. 4. These perforations are arranged in a pattern comprising a plurality of successive courses of perforations, one above another, the perforations in one course not being centered on vertical lines directly above the perforations in the next lower course, the pattern repeating itself at least once over the vertical extent of the perforated sheet 16. (The term "vertical" is used herein to refer to the orientation of the perforated sheet 16 when the package 10 is mounted on a standing pole as illustrated in FIG. 3.) These perforations can be of any shape or size but preferably are uniform in shape and size. In this regard, circular perforations are disclosed in FIG. 1 while rectangular perforations are disclosed in Fig. 4. Typical dimensions would involve dimension A being about ½ inch and dimension B being about ⅛ inch. Typical heights or vertical extents for these perforations are on the average of about 1/16 to ⅛ inch. Typical widths or horizontal extents for these perforations are on the average of about ⅜ inch to about ⅝ inch, preferably about ½ inch. The pattern illustrated in FIG. 4 is an incising pattern that is commonly used in the treatment of standing poles and the like. This pattern as well as other incising patterns that are useful in making perforated sheet 16 are disclosed in Hunt, George M. et al, "Wood Preservation", Second Edition, McGraw-Hill Book Co., Inc. (1953), which is incorporated herein by reference.

As an alternative to securing perforated sheet 16 to flexible sheet 12 using stitching 18, sheet 16 can secured to sheet 12 with any suitable adhesive applied along the marginal edges, sheets 12 and 16, or by heat-sealing the marginal edges of sheets 12 and 16.

Flexible sheet 24 is preferably secured to perforated sheet 16 using a strippable, pressure-sensitive adhesive. The adhesive should be applied substantially over the entire surface of perforated sheet 16 to prevent or inhibit wood-preservative material 14 from coming between flexible sheet 24 and perforated sheet 16. Examples of suitable adhesives include coumarinindene resins, terpene resins, and petroleum hydrocarbon resins (e.g., copolymers of piperidene and tertiary amylene, dicyclopentadiene resins, etc.). Tear strip 28 is attached to sheet 24 and is provided for facilitating the stripping of sheet 24 from sheet 16.

The wood-preservative material 14 can be any wood-preservative material or grease that is commonly used for ground-line treatment of standing poles. These wood-preservative materials typically have a grease-like consistency and preferably contain as the primary active ingredient either copper naphthenate, zinc naphthenate or pentachlorophenol. The wood-preservatives employing copper naphthenate preferably have a copper content of at least about 2% by weight, and the wood-preservatives employing zinc naphthenate preferably have a zinc content of at least about 3% by weight.

The following are specific examples of the wood-preservative materials that are useful with the wood-preservative package 10, all percentages being by weight.

|  | Amount % |
|---|---|
| Example A | |
| Petroleum oil | 65.5 |
| Copper Naphthenate | 20 |
| Mineral Spirits | 5 |
| Cab-O-Sil, (product of Cabot Corp. identified as colloidal silica particles sintered together in chain-like formations) | 8 |
| Triton X-100 (product of Rohm & Haas Co. identified as an ethylene oxide alkyl phenol condensate) | 1.5 |
| Example B | |
| Petroleum oil | 60.5 |
| Copper Naphthenate | 20 |
| Mineral Spirits | 5 |
| Hi Sil T-600, (product of PPG Industries, Inc. identified as hydrated, amorphous silica) | 12 |
| Diethylene glycol | 2.5 |
| Example C | |
| Aromatic Petroleum Derivative Solvent | 81.17 |
| Pentachlorophenol | 9.14 |
| Other chlorinated phenols | 1.07 |

|  | Amount % |
|---|---|
| Inerts | 8.62 |
| Example D | |
| Creosote | 15 |
| Pentachlorophenol | 10 |
| Sodium fluoride | 10 |
| Oils, thickeners, fillers | 65 |
| Example E | |
| Sodium fluoride | 46 |
| Dinitrophenol | 3.4 |
| Potassium dichromate | 2.0 |
| Pentachlorophenol | 0.8 |
| Coal tar | 33 |
| Asbestos | 2.9 |
| Solvent and thickener | 11.9 |
| Example F | |
| Sodium pentachlorophenate | 11 |
| Bituminous pitch | 28.5 |
| Surfactant, clay, water | 60.5 |
| Example G | |
| Sodium fluoride | 21.5 |
| Dinitrophenol | 13.4 |
| Water, tar, oil | 12.2 |
| Arsenious anhydride | 9.6 |
| Pentachlorophenol | 4.3 |
| Other chlorophenols | 0.6 |
| Aromatic petroleum solvents | 3.8 |
| Solvents, binders, cohesives, blending agents | 34.8 |
| Example H | |
| Pentachlorophenol | 8.96 |
| Other chlorophenols and related compounds | 1.04 |
| Coal tar creosote oil | 35.00 |
| Sodium fluoride | 40.00 |
| Potassium dichromate | 3.00 |
| Petroleum solvent | 6.577 |
| Inert ingredients | 5.423 |

Another useful material has been sold under the name "Woodtreat A" (Wood Treating Chemicals Co., St. Louis, Mo.) and is identified as consisting of 87% by weight aromatic petroleum solvent, 10% by weight technical pentachlorophenol, the remainder being emulsifiers, dispersing agents and water.

Another useful wood-preservative material contains a minimum of about 15% by weight creosote, about 15% by weight sodium fluoride or sodium borate, and about 10% by weight pentachlorophenol.

Useful wood-preservative materials are disclosed in U.S. Pat. Nos. 2,875,020 and 2,904,467, these patents being incorporated herein by reference. Breifly, U.S. Pat. No. 2,875,020 discloses the use of a grease-like composition comprising an aromatic oil, a polyvalent metal salt of a $C_{12-18}$ fatty acid and from about 2% to about 15% pentachlorophenol. U.S. Pat. No. 2,904,467 discloses a wood-preservative material which comprises at least 2% pentachlorophenol, 50-95% mineral oil, and a compound of bentonite and an organic nitrogen base in an amount sufficient to impart a grease-like consistency to the preservative material.

Other useful wood-preservative materials are disclosed in DeGroot, Rodney C., "Groundline Treatments of Southern Pine Posts", U.S. Department of Agriculture, Forest Products Laboratory, Research Paper FPL409 (August, 1981), which is incorporated herein by reference.

The wood-preservative package 10 is used by initially separating the flexible sheet 24 from the package 10. This can be done by stripping the flexible sheet 24 from the perforated sheet 16, initially by pulling on tear strip 28. The package 10 is then wrapped around the wood to be preserved with the perforated sheet 16 in contact with the wood to be treated (see FIG. 3). Wood-preservative material 14 passes through perforations 22 to come into contact with and treat the wood. In a preferred embodiment, the perforated sheet 16 is made of a water-soluble material (as discussed above) and after sufficient rainfall the perforated sheet 16 dissolves to permit the wood-preservative material 14 to further contact and treat the wood. An advantage of this invention is that the package 10 can be used without the installer coming into contact with the wood-preservative material 14 and yet the wood-preservative material can effectively contact and treat the wood.

The wood-preservative package 10 is useful in treating wood that is already in place such as standing poles, (e.g., poles used for supporting telephone wires, power transmission lines, and the like) as well as sills, toe plates, stair risers, etc. Referring to FIG. 3, the package 10 is wrapped around the pole 40 at the ground-line 42 using conventional techniques. In this regard, rotten wood and the like is removed from the pole 40 and the package 10 is then nailed or otherwise attached to the pole 40 with the perforated sheet 16 in contact with the pole. In areas of rainfall of about fifteen inches or more a year, the wood-preservative package 10 is preferably wrapped around an area on the pole extending from about six inches above the ground line to about twenty inches below. In arrid regions, the wood-preservative package 10 is perferably wrapped around the pole from approximately the ground-line to as much as three or more feet below the ground-line.

The wood-preservative package 10 is particularly useful in treating poles which show evidence of decay or termite attack at or below the ground-line, but which have a sufficient amount of sound wood to remain in plant for additional use. These packages are also useful in treating salvaged poles that are reused, poles that are moved to a new location, poles where the ground-line has been raised by road grading or filling, poles held in stock for extended periods of time (e.g., one year or longer), and incised butt-treated poles where the treated layer has been damaged so that the untreated wood is exposed.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A wood-preservative package comprising:
   a first flexible sheet;
   a wood-preservative material having a grease-like consistency arranged in a layer upon said first flexible sheet;
   a perforated flexible sheet overlying said preservative material and secured to the marginal edge of said first flexible sheet, the perforations in said perforated flexible sheet being of sufficient number and dimension to permit said wood-preservative material to pass through said perforations, said perforations being arranged in a pattern, said pattern comprising a plurality of successive courses of perforations one above another, the perforations in one course not being centered on vertical lines directly above the perforations in the next lower course, said pattern repeating itself at least once over the vertical extent of said perforated flexible sheet; and another flexible sheet overlying and secured to said perforated flexible sheet.

2. The package of claim 1 with a strippable, pressure-sensitive adhesive between said another flexible sheet and said perforated flexible sheet for securing said another flexible sheet to said perforated flexible sheet.

3. The package of claim 1 wherein said first flexible sheet comprises kraft paper.

4. The package of claim 1 wherein said first flexible sheet comprises kraft paper with a thin flexible coating of a water-insoluble polymeric material applied to at least one side of said kraft paper.

5. The package of claim 1 wherein said first flexible sheet comprises a water-insoluble polymeric material.

6. The package of claim 1 wherein said first flexible sheet comprises polyethylene, polyvinyl chloride or polyvinylidene chloride.

7. The package of claim 1 wherein said perforated flexible sheet comprises a water-soluble polymeric material.

8. The package of claim 1 wherein said perforated flexible sheet comprises polyacrylic acid or a copolymer of an acrylate ester and another hydrophilic monomer.

9. The package of claim 8 wherein said another hydrophilic monomer is hydroxyethyl acrylate, 2-hydroxypropyl acrylate or a mixture thereof.

10. The package of claim 1 wherein said perforated flexible sheet comprises a water-insoluble polymeric material.

11. The package of claim 1 wherein said perforated flexible sheet comprises polyethylene, polyvinyl chloride or polyvinylidene chloride.

12. The package of claim 1 wherein said perforated flexible sheet comprises kraft paper with a thin flexible coating of a water-insoluble polymeric material applied to at least one side of said kraft paper.

13. The package of claim 1 wherein the perforations in said perforated flexible sheet are spaced at regular intervals to permit said wood-preservative material to contact substantially the entire wood surface covered by said wood-preservative package.

14. The package of claim 1 wherein said another flexible sheet comprises kraft paper.

15. The package of claim 1 wherein said another flexible sheet comprises kraft paper with a thin flexible coating of a water-insoluble polymeric material applied to at least one side of said kraft paper.

16. The package of claim 1 wherein said another flexible sheet comprises a water-insoluble polymeric material.

17. The package of claim 1 wherein said another flexible sheet comprises polyethylene, polyvinyl chloride or polyvinylidene chloride.

18. The package of claim 2 wherein said adhesive comprises at least one coumarin-indene resin, at least one terpene resin or at least one petroleum hydrocarbon resin.

19. The package of claim 18 wherein said petroleum hydrocarbon resin comprises at least one copolymer of piperidene and tertiary amylene or at least one dicyclopentadiene resin.

20. The package of claim 1 wherein the marginal edge of said perforated flexible sheet is stitched to the marginal edge of said first flexible sheet.

21. The package of claim 1 wherein the marginal edge of said perforated flexible sheet is secured to the marginal edge of said first flexible sheet with an adhesive or by heat-sealing.

22. The package of claim 1 wherein said preservative material comprises copper naphthenate.

23. The package of claim 1 wherein said preservative material comprises zinc naphthenate.

24. The package of claim 1 wherein said preservative material comprises pentachlorophenol.

25. A method for preserving wood comprising removing said another flexible sheet from the package of claim 1 and wrapping said package around said wood with said perforated flexible sheet in contact with said wood.

26. A method for the ground line treatment of a standing pole comprising removing said another flexible sheet from the package of claim 1 and wrapping said package around said pole with said perforated flexible sheet in contact with said pole.

* * * * *